United States Patent [19]

Shutske

[11] Patent Number: 4,504,669

[45] Date of Patent: Mar. 12, 1985

[54] 1,2-BENZISOXAZOLOXYETHYLAMINES AND INTERMEDIATES FOR THE PREPARATION THEREOF

[75] Inventor: Gregory M. Shutske, Nauheim, Fed. Rep. of Germany

[73] Assignee: Hoechst-Roussel Pharmaceuticals Inc., Somerville, N.J.

[21] Appl. No.: 541,837

[22] Filed: Oct. 14, 1983

Related U.S. Application Data

[63] Continuation of Ser. No. 238,276, Feb. 25, 1981, Pat. No. 4,427,691.

[51] Int. Cl.³ .......................................... C07D 261/20
[52] U.S. Cl. .................................. 548/241; 548/478
[58] Field of Search ............................. 548/241, 478

[56] References Cited

U.S. PATENT DOCUMENTS 4,337,261  6/1982  Shutske et al. ...................... 548/241
4,427,691  2/1984  Schutske ............................. 548/241

FOREIGN PATENT DOCUMENTS 744808  7/1970  Belgium ............................. 548/241
2666    7/1979  European Pat. Off. ............ 548/241

*Primary Examiner*—Donald G. Daus
*Assistant Examiner*—G. Hendricks
*Attorney, Agent, or Firm*—Raymond R. Wittekind

[57] ABSTRACT

Novel 1,2-benzisoxazoloxyethylamines and intermediates for the preparation thereof are described. The 1,2-benzisoxazoloxyethylamines are useful as diuretic agents.

4 Claims, No Drawings

1,2-BENZISOXAZOLOXYETHYLAMINES AND INTERMEDIATES FOR THE PREPARATION THEREOF

This is a continuation of application Ser. No. 238,276 filed Feb. 25, 1981 now U.S. Pat. No. 4,427,691.

DESCRIPTION OF THE INVENTION

The present invention relates to novel 1,2-benzisoxazoloxyethylamines. More particularly, the present invention relates to 1,2-benzisoxazoloxyethylamines of the formula:

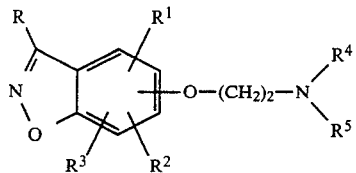

wherein R is

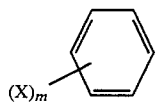

wherein X is hydrogen, halogen, loweralkyl, loweralkoxy, loweralkylthio or trifluoromethyl; $R^1$, $R^2$ and $R^3$ are each independently hydrogen, halogen or methyl; $R^4$ and $R^5$ are each independently hydrogen or loweralkyl; m is 1, 2 or 3; and the pharmaceutically acceptable acid addition salts thereof, which are useful as diuretic agents alone or in combination with inert diuresis-producing adjuvants.

Preferred diuretic 1,2-benzisoxazoloxyethylamines of the present invention are those compounds wherein X is halogen, $R^1$, $R^2$ and $R^3$ are each independently hydrogen, methyl or halogen; m is 1 or 2 and the

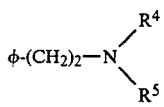

group is bound to the 6-position of the 1,2-benzisoxazole nucleus.

Most preferred diuretic 1,2-benzisoxazoloxyethylamines of the present invention are those compounds wherein X is 2-fluoro, $R^1$ and $R^2$ are hydrogen; $R^3$ is chloro or methyl; $R^4$ and $R^5$ are each independently hydrogen or loweralkyl; the

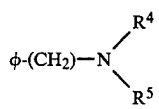

group is bound to the 6-position of the 1,2-benzisoxazole nucleus; and the $R^3$ group is bound to the 7-position of the 1,2-benzisoxazole nucleus.

The present invention also relates, more particularly, to 2-haloethoxy-1,2-benzisoxazoles of the formula

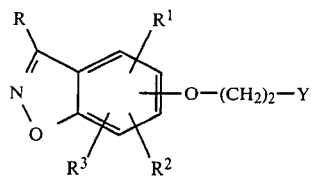

wherein R is

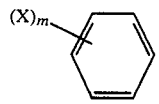

wherein X is hydrogen, halogen, loweralkyl, loweralkoxy, loweralkylthio or trifluoromethyl; $R^1$, $R^2$ and $R^3$ are each independently hydrogen, halogen or methyl; Y is halogen; and m is 1, 2 or 3, 2-phthalimidoethoxy-1,2-benzisoxazoles of the formula

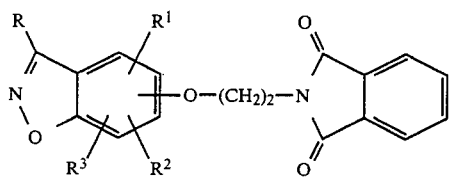

wherein R is

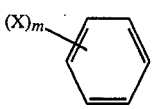

wherein X is hydrogen, halogen, loweralkyl, loweralkoxy, loweralkylthio or trifluoromethyl. $R^1$, $R^2$ and $R^3$ are each independently hydrogen, halogen or methyl; m is 1, 2 or 3; and 1,2-benzisoxazoloxyethylalkanamides of the formula

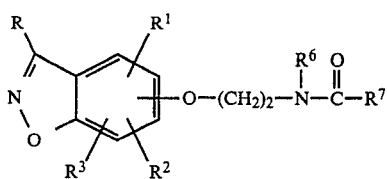

wherein R is

wherein X is hydrogen, halogen, loweralkyl, loweralkoxy, loweralkylthio or trifluoromethyl; $R^1$, $R^2$ and $R^3$ are each independently hydrogen, halogen or methyl; $R^6$ is hydrogen or loweralkyl, $R^7$ is hydrogen or loweralkyl; and m is 1, 2 or 3, useful as intermediates for the preparation of the hereinbeforementioned 1,2-benzisoxazoloxyethylamines.

Subgeneric to the intermediate 2-haloethoxy-1,2-benzisoxazoles of the present invention are compounds wherein X is halogen, $R^1$, $R^2$ and $R^3$ are each independently hydrogen, methyl or halogen; m is 1 or 2; Y is chloro or bromo and the $O-(CH_2)_2-Y$ group is bound to the 6-position of the 1,2-benzisoxazole nucleus, and compounds wherein X is 2-fluoro, $R^1$ and $R^2$ are hydrogen; $R^3$ is chloro or methyl; Y is bromo; the $\phi-(CH_2)_2-Y$ group is bound to the 6-position of the 1,2-benzisoxazole nucleus; and the $R^3$ group is bound to the 7-position of the 1,2-benzisoxazole nucleus.

Subgeneric to the intermediate 2-phthalimidoethoxy-1,2-benzisoxazoles of the present invention are compounds wherein X is halogen; $R^1$, $R^2$ and $R^3$ are each independently hydrogen, methyl or halogen; m is 1 or 2; the

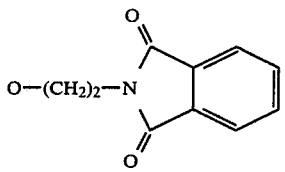

group is bound to the 6-position of the 1,2-benzisoxazole nucleus and compounds wherein X is 2-fluoro, $R^1$ and $R^2$ are hydrogen; $R^3$ is chloro or methyl; and the

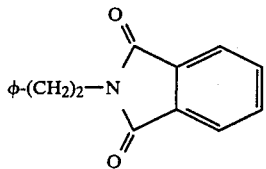

group is bound to the 6-position of the 1,2-benzisoxazole nucleus; and the $R^3$ group is bound to the 7-position of the 1,2-benzisoxazole nucleus.

Subgeneric to the intermediate 1,2-benzisoxazoloxyethylalkanamides of the present invention are compounds wherein X is halogen, $R^1$, $R^2$ and $R^3$ are each independently hydrogen, methyl or halogen, m is 1 or 2; and the

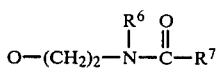

group is bound to the 6-position of the 1,2-benzisoxazole nucleus and compounds wherein X is 2-fluoro, $R^1$ and $R^2$ are hydrogen; $R^3$ is chloro or methyl; $R^6$ is hydrogen, $R^7$ is methyl; the

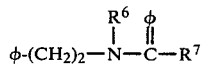

group is bound to the 6-position of the 1,2-benzisoxazole nucleus; and the $R^3$ group is bound to the 7-position of the 1,2-benzisoxazole nucleus.

As used throughout the specification and appended claims, the terms "alkyl" refers to a straight or branched chain hydrocarbon radical containing no unsaturation and having 1 to 10 carbon atoms such as methyl, ethyl, n-propyl, i-propyl, tert-butyl, hexyl, octyl, decyl and the like; the term "alkoxy" refers to a monovalent substituent which consists of an alkyl group linked through an ether oxygen and having its free valence bond from the ether oxygen such as methoxy, ethoxy, isopropoxy, tert-butoxy, hexoxy, octoxy, decoxy and the like; the term "alkylthio" refers to a monovalent substituent which consists of an alkyl group linked through a thio sulfur and having its free valence from the thio sulfur such as methylthio, ethylthio, isopropylthio, tert-butylthio, hexylthio, octylthio, decylthio and the like; the term "alkanol" refers to a compound formed by combination of an alkyl group and hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "alkanoic acid anhydride" refers to a compound formed by the loss of the elements of water from two alkanoic acids. Examples of alkanoic acid anhydrides are formic anhydride, acetic anhydride, propanoic anhydride, 2,2-dimethylacetic anhydride, hexanoic anhydride, octanoic anhydride, decanoic anhydride and the like; the term "alkanamide" refers to a compound formed by replacement of the hydroxy function of an alkanoic acid with an amino or substituted amino moiety. Examples of "alkanamides" are formamide, acetamide, propanamide, 2,2-dimethylacetamide, hexanamide, octanamide, decanamide and the like; the term "halogen" refers to a member of the family consisting of fluorine, chlorine, bromine or iodine. The term "alkali metal" refers to a member of the group consisting of lithium, sodium and potassium. The term "lower" as applied to any of the aforemention groups refers to a group having a carbon skeleton containing up to and including 6 carbon atoms.

The compounds of the present invention which lack an element of symmetry exist as optical antipodes and as the racemic forms thereof. The optical antipode may be prepared from the corresponding racemic forms by standard optical resolution techniques, involving, for example, the separation of disasteromeric salts of those instant compounds characterized by the presence of an amino group and an optically active acid, or by the synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel compounds of the present invention may be prepared from hydroxy-1,2-benzisoxazoles of Formula I by the reactions illustrated in the Reaction Scheme.

In the initial step, the hydroxy-1,2-benzisoxazole I is converted to the 2-haloethoxy-1,2-benzisoxazole II. The conversion is conveniently performed by generating the phenoxide of I with a strong base such as, for example, sodium or potassium hydride, in a polar aprotic solvent such as, for example, dimethylacetamide, dimethylformamide or hexamethylphosphoramide, and contacting the phenxoide so formed with a haloethylhalide of the formula

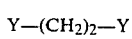

wherein Y is halogen. Sodium hydride is the preferred base and dimethylformamide is the preferred solvent.

The temperatures at which the phenoxide is generated and the condensation is affected are not narrowly critical. It is, however, preferred to generate the phenoxide at ambient temperature (about 25° C.) and to contact the phenoxide with the haloethylhalide at an elevated temperature within the range of about 75°-125° C., a reaction temperature of about 100° being more preferred.

In the second step of the sequence, the 2-haloethoxy-1,2-benzisoxazole II is condensed with an alkali metal salt, such as the sodium or potassium salt of phthalimide in a polar aprotic solvent to afford the 2-phthalimidoethoxy-1,2-benzisoxazole III. Suitable polar aprotic solvents are dimethylacetamide, dimethylformamide and hexamethylphosphoramide. Potassium phthalimide is the preferred alkali metal. Dimethylformamide is the preferred solvent. The condensation is preferably performed at a temperature of about 75° ot 105°, at which it proceeds at a reasonable rate. A condensation temperature of about 90° C. is more preferred.

In the third step of the sequence, the step leading to primary 1,2-benzisoxazoloxyethylamines of Formula IV wherein $R^4$ and $R^5$ are hydrogen, the 2-phthalimido-ethoxy-1,2-benzisoxazole II is cleaved by hydrazine, preferrably in the form of its hydrate, in a suitable solvent selected from the alkanols, methanol, ethanol, 2-propanol and the like, at the reflux temperature of the system. At this temperature, which is not critical, the cleavage proceeds at a reasonable rate.

In the step leading to secondary 1,2-benzisoxazoloxyethylamines of Formula IV wherein $R^4$ is hydrogen and $R^5$ is loweralkyl, primary 1,2-benzisoxazoloxyethylamines of formula IV wherein $R^4$ and $R^5$ are hydrogen are acylated with an alkanoic acid of the formula

wherein $R^7$ is hydrogen or loweralkyl, or the corresponding anhydride thereof of the formula

wherein $R^7$ is as above to provide alkanamides of formula V wherein $R^1$, $R^2$ and $R^3$ and n are as above, $R^6$ is hydrogen and $R^7$ is loweralkyl. The acylation is generally accomplished by contacting the primary amine IV ($R^4$ and $R^5$ are hydrogen) with an alkanoic acid anhydride, preferably at an elevated temperature of about 90°-150° C. in the presence of a mineral acid, such as, for example hydrochloric acid or sulfuric acid (or a mineral acid salt of the amine may be employed). Hydrochloric acid (or amine hydrochloride) and steam bath temperatures are more preferred.

When the acylation is performed utilizing an alkanoic acid, temperatures in the range of about 90°-250° are preferred. With higher molecular weight alknaoic acids, higher temperatures are usually required.

The alkanamide V ($R^6$ is hydrogen and $R^7$ is loweralkyl), obtained as described above, may be reduced to the desired secondary 1,2-benzisoxazoloxyethylamines by methods well-known in the art. For example, alkanamides V ($R^6$ is hydrogen and $R^7$ is hydrogen or loweralkyl) may be reduced with lithium aluminum hydride in an ethereal solvent such as diethyl ether or tetrahydrofuran to secondary amines having the same carbon content. See R. B. Wagner and H. D. Zook, "Synthetic Organic Chemistry", John Wiley and Sons, Inc., New York, N.Y., 1953, page 660.

Tertiary 1,2-benzisoxazoloxyethylamines of formula IV wherein $R^4$ and $R^5$ are alkyl may be prepared by acylating secondary 1,2-benzisoxazoloxyethylamines of formula IV wherein $R^4$ is hydrogen and $R^5$ is alkyl and reducing the alkanamides of formula V wherein $R^6$ is alkyl and $R^7$ is hydrogen or alkyl, so formed, by methods hereinbefore described.

The 1,2-benzisoxazoloxyethylamines of the present invention are useful as diuretics due to their ability to produce diuresis in mammals.

Diuretic activity is determined in rats by a method similar to that described by C. M. Kagawa and M. J. Kalm, Arch. Intern. Pharmacodyn., 137, 241 (1962). The test compound is administered orally to a group of rats and the average volume of urine excreted is measured. One gram per kilogram of body weight of urea, a known diuretic agent, is administered orally to a positive control group of rats and the average volume of urine excreted is measured. Diuretic activity expressed as the ratio of the average volume of urine excreted in the test group to the average volume of urine excreted in the control group (a ratio greater than 1 indicates diuretic activity) of some of the instant 1,2-benzisoxazoloxyethylamines as well as standard diuretics is presented in Table I.

TABLE I

| COMPOUND | DOSE (mg/kg of body weight) | DIURESIS PRODUCTION (test compound volume/urea volume) |
|---|---|---|
| 2-{7-chloro-3-(2-fluorophenyl)-1,2-benzisoxazol-6-yl]oxy}ethylamine hydrochloride | 64 | 3.3 |
| ethacrynic acid | 64 | 2.5 |
| tienilic acid | 64 | 1.8 |

Diuresis production is achieved when the present 1,2-benzisoxazoloxyethylamines are administered to a subject requiring such treatment as an effective oral, parenteral or intravenous dose of from 0.01 to 100 mg/kg of body weight per day. A particulary effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Effective amounts of 1,2-benzisoxazoloxyethylamines of the present invention may be administered to a subject by any one of various methods, for example, orally as in capsules or tablets, parenterally in the form of sterile solutions or suspensions, and in some cases intravenously in the form of sterile solutions. The 1,2-benzisoxazoloxyethylamines of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

The 1,2-benzisoxazoloxyethylamines of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of the 1,2-benzisoxazoloxyethylamines of the present invention, but may be varied depending upon the particular form and may conveniently be between 4% to about 70% of the weight of the unit. The amount of present compound in such composition is such that a suitable dosage will be obtained. Preferred compositions and preparations according to the present invention are prepared so that an oral dosage unit form contains between 1.0–300 milligrams of the 1,2-benzisoxazoloxyethylamines.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present 1,2-benzisoxazoloxyethylamines, sucrose as a sweetening agent and certain preservatives, dyes and colorings and flavors. Materials used in preparing these various compositions should be pharmaceutically pure and nontoxic in the amounts used.

For the purposes of parenteral therapeutic administration, the 1,2-benzisoxazoloxyethylamines of the present invention may be incorporated into a solution or suspension. These preparations should contain at least 0.1% of the aforesaid compound, but may be varied to be between 0.5 and about 30% of the weight thereof. The amount of the present compound in such compositions is such that a suitable dosage will be obtained. Preferred compositions and preparations according to the present invention are prepared so that a parenteral dosage unit contains between 0.5 to 100 milligrams of the 1,2-benzisoxazoloxyethylamines.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The present invention is illustrated by the following examples, which illustration is not be be construed as limiting the invention described herein. All temperatures are given in degrees centigrade.

EXAMPLE 1

7-Chloro-3-(2-fluorophenyl)-6-(2-bromoethoxy)-1,2-benzisoxazole

7-Chloro-6-hydroxy-3-(2-fluorophenyl)-1,2-benzisoxazole (13.06 g) is dissolved in 50 ml of dimethylformamide and treated with 1.32 g of 99% sodium hydride. The solution is added dropwise to a solution of 1,2-dibromoethane (28.0 g) in 50 ml of dimethylformamide, preheated to 100°. After 2 hrs, an additional 1.0 g of sodium hydride and 22 g of dibromoethane are added. The reaction is stirred for 1 hr at 100° and overnight at room temperature. The reaction mixture is then poured into water and extracted with ethyl acetate. Drying and evaporation gives a solid which is washed with ether to give 9.20 g of product, mp, 131°–133°. Additional product, mp 131°–132°, is obtained by chromatography of the residue obtained from the ether washes over silica gel using dichloromethane as the eluent. The combined yield is 11.3 g. The analytical sample is recrystallized from toluene and has mp 133°–134°.

ANALYSIS: Calculated for $C_{15}H_{10}BrClFNO_2$: 48.61%C; 2.72%H; 3.78%N; Found: 48.74%C; 2.76%H; 3.73%N.

EXAMPLE 2

7-Chloro-3-(2-fluorophenyl)-6-(2-phthalimidoethoxy)-1,2-benzisoxazole

7-Chloro-3-(2-fluorophenyl)-6-(2-bromoethoxy)-1,2-benzisoxazole (11.3 g) is warmed at 90° in 60 ml of dimethylformamide with potassium phthalimide (6.5 g). After 3 hrs, the reaction is poured into water and the product is extracted into dichloromethane. The dried organic phase is evaporated and the residue is washed with ether to give 10.7 (82%) of product, mp 166°–168°. The analytical sample is recrystallized from chloroform/ether and has mp 169°–171°.

ANALYSIS: Calculated for $C_{23}H_{14}ClFN_2O_4$: 63.24%C; 6.41%N; Found: 63.05%C; 3.16%H; 6.32%N.

EXAMPLE 3

2-{[7-Chloro-3-(2-fluorophenyl)-1,2-benzisoxazol-6-yl]oxy}ethylamine hydrochloride 7-Chloro-3-(2-fluorophenyl)-6-(2-phthalimidoethoxy)-1,2-benzisoxa zole (8.0 g) is heated under reflux for 4 hrs in 75 ml of methanol containing 1.3 g of 85% hydrazine hydrate. The solid is filtered and the methanol is evaporated. The combined solids are distributed between water and ethyl acetate. The organic phase is dried and concentrated under reduced pressure to give 5.30 g (87%) as a glass that crystallizes slowly. The hydrochloride forms smoothly in ether with a trace of methanol as crystals, mp 235°–240°. The analytical sample is recrystallized from propanol/methanol and has mp 240°–243°.

ANALYSIS: Calculated for $C_{15}H_{12}ClFN_2O_2HCl$: 52.49%C; 3.83%H; 8.16%N; Found: 52.72%C; 3.78%H; 8.18%N.

By employing the following 6-hydroxy-1,2-benzisoxazoles, the preparation of which is described in U.S. patent application Ser. No. 201,083, filed Oct. 27, 1981:

1. 7-chloro-3-(2,6-difluorophenyl)-6-hydroxy-1,2-benzisoxazole;
2. 7-chloro-3-(2,4-difluorophenyl)-6-hydroxy-1,2-benzisoxazole;
3. 5-chloro-3-(2-fluorophenyl)-6-hydroxy-1,2-benzisoxazole;
4. 3-(2-fluorophenyl)-6-hydroxy-1,2-benzisoxazole;
5. 3-(2-fluorophenyl)-6-hydroxy-7-methyl-1,2-benzisoxazole;
6. 3-(2-fluorophenyl)-6-hydroxy-7-iodo-1,2-benzisoxazole;
7. 7-chloro-6-hydroxy-3-(2,3-difluorophenyl)-1,2-benzisoxazole;
8. 7-chloro-6-hydroxy-3-(2-difluorophenyl)-1,2-benzisoxazole;
9. 7-chloro-3-(2,5-difluorophenyl)-6-hydroxy-1,2-benzisoxazole;
10. 5,7-dichloro-3-(2-fluorophenyl)-6-hydroxy-1,2-benzisoxazole;
11. 4-chloro-3-(2-fluorophenyl)-6-hydroxy-1,2-benzisoxazole;
12. 7-chloro-3-(3-fluorophenyl)-1,2-benzisoxazole;
13. 3-(2-fluorophenyl)-6-hydroxy-4,5,7-trichloro-1,2-benzisoxazole;
14. 7-chloro-3-(4-chloro-2-fluorophenyl)-6-hydroxy-1,2-benzisoxazole;
15. 3-(2,5-difluorophenyl)-6-hydroxy-1,2-benzisoxazole;
16. 3-(2,6-difluorophenyl)-6-hydroxy-1,2-benzisoxazole;
17. 3-(4-chlorophenyl)-6-hydroxy-1,2-benzisoxazole; and
18. 7-chloro-3-(2-ethoxy-4-fluorophenyl)-6-hydroxy-1,2-benzisoxazole;

and following the procedures described in Examples 1 to 3, there may be prepared, respectively, the following 1,2-benzisoxazoloxyethylamines:

1A. 2-{[7-chloro-3-(2,6-difluorophenyl)-1,2-benzisoxazol-6-yl]oxy}ethylamine;
2A. 2-{[7-chloro-3-(2,4-difluorophenyl)-1,2-benzisoxazol-6-yl]oxy}ethylamine;
3A. 2-{[5-chloro-3-(2-fluorophenyl)-1,2-benzisoxazol-6-yl]oxy}ethylamine;
4A. 2-{[3-(2-fluorophenyl)-1,2-benzisoxazol-6-yl]oxy}ethylamine;
5A. 2-{[3-(2-fluorophenyl)-7-methyl-1,2-benzisoxazol-6-yl]oxy}ethylamine;
6A. 2-{[3-(2-fluorophenyl)-7-iodo-1,2-benzisoxazol-6-yl]oxy}ethylamine;
7A. 2-{[7-chloro-3-(2,3-difluorophenyl)-1,2-benzisoxazol-6-yl]oxy}ethylamine;
8A. 2-{[7-chloro-3-(2-fluorophenyl)-1,2-benzisoxazol-6-yl]oxy}ethylamine;
9A. 2-{[7-chloro-3-(2,5-difluorophenyl)-1,2-benzisoxazol-6-yl]oxy}ethylamine;
10A. 2-{[5,7-dichloro-3-(2-fluorophenyl)-1,2-benzisoxazol-6-yl]oxy}ethylamine;
11A. 2-{[4-chloro-3-(2-fluorophenyl)-1,2-benzisoxazol-6-yl]oxy}ethylamine;
12A. 2-{[7-chloro-3-(3-fluorophenyl)-1,2-benzisoxazol-6-yl]oxy}ethylamine;
13A. 2-{[3-(2-fluorophenyl)-4,5,7-trichloro-1,2-benzisoxazol-6-yl]oxy}ethylamine;
14A. 2-{[7-chloro-3-(4-chloro-2-fluorophenyl)-1,2-benzisoxazol-6-yl]oxy}ethylamine;
15A. 2-{[3-(2,5-difluorophenyl)-1,2-benzisoxazol-6-yl]oxy}ethylamine;
16A. 2-{[3-(2,6-difluorophenyl)-1,2-benzisoxazol-6-yl]oxy}ethylamine;
17A. 2-{[3-(4-chlorophenyl)-1,2-benzisoxazol-6-yl]oxy}ethylamine;
18A. 2-{[7-chloro-3-(2-ethoxy-4-fluorophenyl)-1,2-benzisoxazol-6-yl]oxy}ethylamine;

via the following 2-haloethoxy-1,2-benzisoxazoles:

1B. 7-chloro-3-(2,6-difluorophenyl)-6-(2-bromoethoxy)-1,2-benzisoxazole;
2B. 7-chloro-3-(2,4-difluorophenyl)-6-(2-bromoethoxy)-1,2-benzisoxazole;
3B. 5-chloro-3-(2-fluorophenyl)-6-(2-bromoethoxy)-1,2-benzisoxazole;
4B. 3-(2-fluorophenyl)-6-(2-bromoethoxy)-1,2-benzisoxazole;
5B. 3-(2-fluorophenyl)-7-methyl-6-(2-bromoethoxy)-1,2-benzisoxzole;
6B. 3-(2-fluorophenyl)-7-iodo-6-(2-bromoethoxy)-1,2-benzisoxazole;
7B. 7-chloro-3-(2,3-difluorophenyl)-6-(2-bromoethoxy)-1,2-benzisoxazole;
8B. 7-chloro-3-(2-fluorophenyl)-6-(2-bromoethoxy)-1,2-benzisoxazole;
9B. 7-chloro-3-(2,5-difluorophenyl)-6-(2-bromoethoxy)-1,2-benzisoxazole;
10B. 5,7-dichloro-3-(2-fluorophenyl)-6-(2-bromoethoxy)-1,2-benzisoxazole;
11B. 4-chloro-3-(2-fluorophenyl)-6-(2-bromoethoxy)-1,2-benzisoxazole;
12B. 7-chloro-3-(3-fluorophenyl)-6-(2-bromoethoxy)-1,2-benzisoxazole;
13B. 3-(2-fluorophenyl)-4,5,7-trichloro-6-(2-bromoethoxy)-1,2-benzisoxazole;
14B. 7-chloro-3-(4-chloro-2-fluorophenyl)-6-(2-bromoethoxy)-1,2-benzisoxazole;
15B. 3-(2,5-difluorophenyl)-6-(2-bromoethoxy)-1,2-benzisoxazole;
16B. 3-(2,6-difluorophenyl)-6-(2-bromoethoxy)-1,2-benzisoxazole;
17B. 3-(4-chlorophenyl)-6-(2-bromoethoxy)-1,2-benzisoxazole; and
18B. 7-chloro-3-(2-ethoxy-4-fluorophenyl)-6-(2-bromoethoxy)-1,2-benzisoxazole;

and the following 2-phthalimidoethoxy-1,2-benzisoxazoles:

1C. 7-chloro-3-(2,6-difluorophenyl)-6-(2-phthalimidoethoxy)-1,2-benzisoxazole;
2C. 7-chloro-3-(2,4-difluorophenyl)-6-(2-phthalimidoethoxy)-1,2-benzisoxazole;
3C. 5-chloro-3-(2-fluorophenyl)-6-(2-phthalimidoethoxy)-1,2-benzisoxazole;
4C. 3-(2-fluorophenyl)-6-(2-phthalimidoethoxy)-1,2-benzisoxazole;
5C. 3-(2-fluorophenyl)-7-methyl-6-(2-phthalimidoethoxy)-1,2-benzisoxazole;
6C. 3-(2-fluorophenyl)-7-iodo-6-(2-phthalimidoethoxy)-1,2-benzisoxazole;
7C. 7-chloro-3-(2-difluorophenyl)-6-(2-phthalimidoethoxy)-1,2-benzisoxazole;
8C. 7-chloro-3-(2-fluorophenyl)-6-(2-phthalimidoethoxy)-1,2-benzisoxazole;
9C. 7-chloro-3-(2,5-difluorophenyl)-6-(2-phthalimidoethoxy)-1,2-benzisoxazole;

10C. 5,7-dichloro-3-(2-fluorophenyl-6-(2-phthalimidoethoxy)-1,2-benzisoxazole;
11C. 4-chloro-3-(2-fluorophenyl-6-(2-phthalimidoethoxy)-1,2-benzisoxazole;
12C. 7-chloro-3-(3-fluorophenyl-6-(2-phthalimidoethoxy)-1,2-benzisoxazole;
13C. 3-(2-fluorophenyl)-4,5,7-trichloro-6-(2-phthalimidoethoxy)-1,2-benzisoxazole;
14C. 7-chloro-3-(4-chloro-2-fluorophenyl)-6-(2-phthalimidoethoxy)-1,2-benzisoxazole;
15C. 3-(2,5-difluorophenyl)-6-(2-phthalimidoethoxy)-1,2-benzisoxazole;
16C. 3-(2,6-difluorophenyl)-6-(2-phthalimidoethoxy)-1,2-benzisoxazole;
17C. 3-(4-chlorophenyl)-6-(2-phthalimidoethoxy)-1,2-benzisoxazole; and
18C. 7-chloro-3-(2-ethoxy-4-fluorophenyl)-6-(2-phthalimidoethoxy)-1,2-benzisoxazole.

By utilizing the teachings of U.S. patent application Ser. No. 201,083, filed Oct. 27, 1981, and employing the methods described in Examples 1 to 3 of this specification, the following 1,2-benzisoxazoloxyethylamines may be prepared:
1. 2-{[7-chloro-3-(4-tolyl)-1,2-benzisoxazol-6-yl]oxy}-ethylamine;
2. 2-{[7-chloro-3-(2-tolyl)-1,2-benzisoxazol-6-yl]oxy}-ethylamine;
3. 2-{[7-chloro-3-(2-trifluoromethyl)-1,2-benzisoxazol-6-yl]oxy}ethylamine;
4. 2-{[7-chloro-3-(2-methylthiophenyl)-1,2-benzisoxazol-6-yl]oxy}ethylamine;
5. 2-{[7-methyl-3-(2-fluorophenyl)-benzasoxazol-6-yl]oxy}ethylamine;
6. 3-{[7-chloro-3-(2,4,6-trifluoromethyl-1,2-benzisoxazol-6-yl]oxy}ethylamine;
7. 2-{[7-chloro-3-phenyl-1,2-benzisoxazol-6-yl]oxy}-ethylamine;
8. 2-{[7-chloro-3-(2-fluorophenyl)-7-(2-bromoethoxy)-1,2-benzisoxazol-6-yl]oxy}ethylamine;
9. 7-bromo-2-{[3-(2-fluorophenyl)-1,2-benzisoxazol-6-yl]-oxy}ethylamine; and
10. 2-{[7-bromo-3-(2,6-difluorophenyl)-1,2-benzisoxazol-6-yl]oxy}ethylamine, via the following 2-halethoxy-1,2-benzisoxazoles:
1A. 7-chloro-3-(4-tolyl)-6-(2-bromoethoxy)-1,2-benzisoxazole;
2A. 7-chloro-3-(2-tolyl)-6-(2-bromoethoxy)-1,2-benzisoxazole;
3A. 7-chloro-3-(2-trifluoromethylphenyl)-6-(2-bromoethoxy-1,2-benzisoxazole;
4A. 7-chloro-3-(2-methylthiophenyl)-6-(2-bromoethoxy)-1,2-benzisoxazole;
5A. 7-methyl-3-(2-fluorophenyl)-6-(2-bromoethoxy)-1,2-benzisoxazole;
6A. 7-chloro-3-(2,4,6-trifluorophenyl)-6-(2-bromoethoxy)-1,2-benzisoxazole;
7A. 7-chloro-3-phenyl-6-(2-bromoethoxy)-1,2-benzisoxazole;
8A. 7-chloro-3-(2-fluorophenyl)-7-(2-bromoethoxy)-1,2-benzisoxazole;
9A. 7-bromo-3-(2-fluorophenyl)-6-(2-bromoethoxy)-1,2-benzisoxazole; and
10A. 7-bromo-3-(2,6-difluorophenyl)-6-(2-bromoethoxy-1,2-benzisoxazole.
and the following 2-phthalimidoethoxy-1,2-benzisoxazoles:
1B. 7-chloro-3-(4-tolyl)-6-(2-phthalimidoethoxy)-1,2-benzisoxazole;
2B. 7-chloro-3-(2-tolyl)-6-(2-phthalimidoethoxy)-1,2-benzisoxazole;
3B. 7-chloro-3-(2-trifluoromethylphenyl)-6-(2-phthalimidoethoxy)-1,2-benzisoxazole;
4B. 7-chloro-3-(2-methylthiophenyl)-6-(2-phthalimidoethoxy)-1,2-benzisoxazole;
5B. 7-methyl-3-(2-fluorophenyl)-6-(2-phthalimidoethoxy)-1,2-benzisoxazole;
6B. 7-chloro-3-(2,4,6-trifluorophenyl)-6-(2-phthalimidoethoxy)-1,2-benzisoxazole;
7B. 7-chloro-3-phenyl-6-(2-phthalimidoethoxy)-1,2-benzisoxazole;
8B. 7-chloro-3-(2-fluorophenyl)-5-(2-phthalimidoethoxy)-1,2-benzisoxazole;
9B. 7-bromo-3-(2-fluorophenyl)-6-(2-phthalimidoethoxy)-1,2-benzisoxazole; and
10B. 7-bromo-3-(2,6-difluorophenyl)-6-(2-phthalimidoethy)-1,2-benzisoxazole.

EXAMPLE 4

N-{2-[[7-chloro-(2-fluorophenyl)-1,2-benzisoxazol-6-yl]oxy]ethyl}acetamide

2-{[7-Chloro-3-(2-fluorophenyl-1,2-benzisoxazol-6-yl]oxy}ethylamine hydrochloride (5.10 g) is warmed on a steam bath for 30 min with 25 ml of acetic anhydride. The reaction mixture is evaporated under reduced pressure and the residue is treated with warm 5% sodium bicarbonate. The solid is filtered and recrystallized from toluene to give 4.76 g (82%) of product, mp 154°–155°.
ANALYSIS: Calculated for $C_{17}H_{14}ClFN_2O_3$: 58.54%C; 4.05%H; 8.03%N; Found: 58.80%C; 4.02%H; 7.80%N.

By employing 1,2-benzisoxazoloxyethylamines enumerated under Example 3 and utilizing the methods described in Example 4 and taught on pages 8 and 9 of the specification, the following 1,2-benzisoxazoloxyethylalkanamides, among others, may be prepared:
1. N-{2-[[7-chloro-3-(2,6-difluorophenyl)-1,2-benzisoxazol-6-yl]oxy]ethyl}-N-methylacetamide;
2. N-{2-[[7-chloro-3-(4-tolyl)-1,2-benzisoxazol-6-yl]oxy]ethyl}formamide;
3. N-{2-[[7-chloro-3-(2-ethoxy-4-fluorophenyl)-1,2-benzisoxazol-6-yl]oxy]ethyl-N-ethylproponamide;
4. N-{2-[[7-chloro-3-(2-trifluoromethyl-1,2-benzisoxazol-6-yl]oxy]ethyl}acetamide;
5. N-{2-[[7-chloro-3-(2-methylthiophenyl)-1,2-benzisoxazol-6-yl]oxy]ethyl}formamide;
6. N-{2-[[7-chloro-3-phenyl-1,2-benzisoxazol-6-yl]oxy]ethyl}-N-methylformamide;
7. N-{2-[[3-(2-fluorophenyl)-7-methyl-1,2-benzisoxazol-6-yl]oxy]ethyl}-N-ethylformamide;
8. N-{2-[[7-chloro-3-(2,4,6-triflouromethyl-1,2-benzisoxazol-6-yl-]oxy]ethyl}N-ethylacetamide; and
9. N-{2-[[3-(2-fluorophenyl)-1,2-benzisoxazol]-7-yl]-ethyl}acetamide.

By utilizing the teachings presented on page 9 of the specification, the following secondary and tertiary 1,2-benzisoxazoloxyethylamines may be prepared:
1. N-2-{[7-chloro-3-(2-fluorophenyl)-1,2-benzisoxazol-6-yl]ethyl}-N-ethylamine;
2. N-2-{[7-chloro-3-(2-fluorophenyl)-1,2-benzisoxazol-6-yl]oxy}ethyl-N-ethyl-N-methylamine;
3. N-2-{[7-chloro-3-(2-fluorophenyl)-1,2-benzisoxazol-6-yl]oxy}propyl-N,N-dipropylamine; and
4. N-2-{[7-chloro-3-(2-fluorophenyl)-1,2-benzisoxazol-7-yl]oxy}ethylamine.

REACTION SCHEME

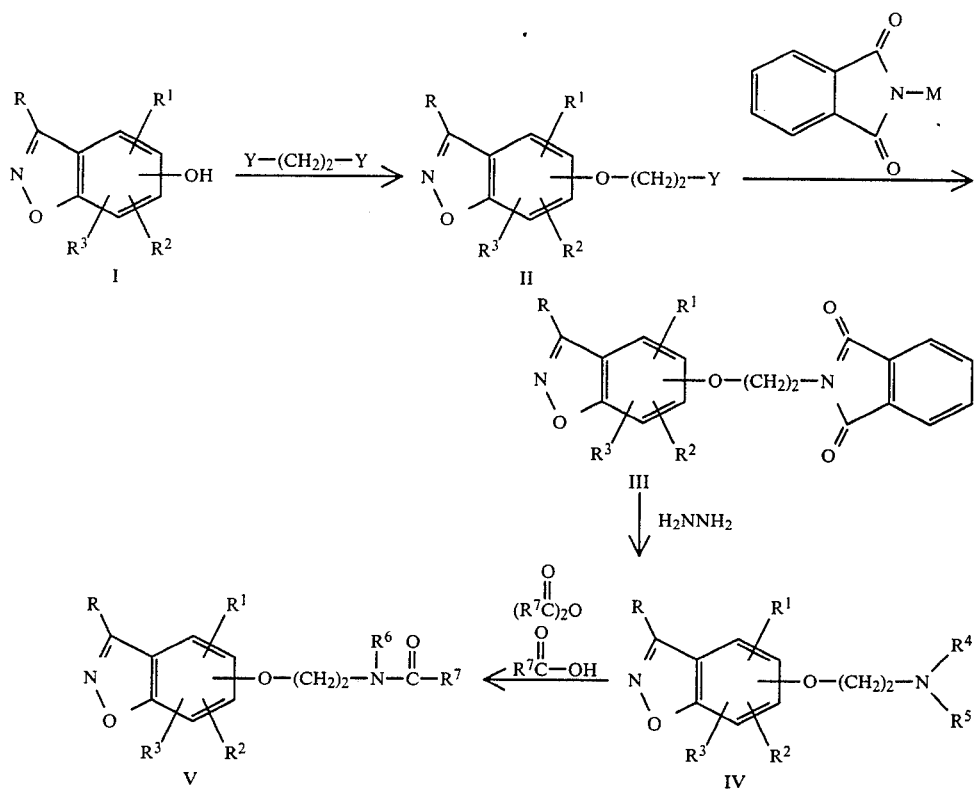

I claim:
1. A compound of the formula

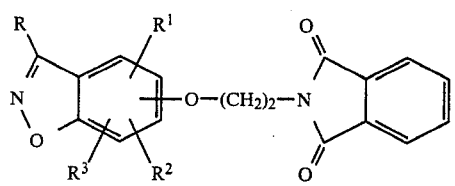

wherein R is

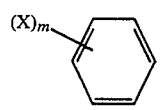

wherein X is hydrogen, halogen, loweralkyl, loweralkoxy, loweralkylthio or trifluoromethyl; $R^1$, $R^2$ and $R^3$ are each independently hydrogen, halogen or methyl; and m is 1, 2 or 3.

2. The compound of claim 1 wherein X is halogen; $R^1$, $R^2$ and $R^3$ are each independently hydrogen, methyl or halogen; m is 1 or 2; and the

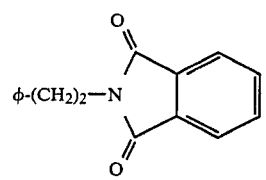

group is bound to the 6-position of the 1,2-benzisoxazole nucleus.

3. The compound of claim 2 wherein X is 2-fluoro, $R^1$ and $R^2$ are hydrogen; $R^3$ is chloro or methyl; and the $R^3$ group is bound to the 7-position of the 1,2-benzisoxazole nucleus.

4. The compound of claim 3 which is 7-chloro-3-(2-fluorophenyl)-6-[(2-phthalimidoethoxy)]-1,2-benzisoxazole.

* * * * *

UNITED STATES PATENT AND TRADEMARK OFFICE
CERTIFICATE OF CORRECTION

PATENT NO.   : 4,504,669
DATED        : March 12, 1985
INVENTOR(S)  : Gregory M. Shutske It is certified that error appears in the above-identified patent and that said Letters Patent is hereby corrected as shown below:

Column 5, Line 61

"alknaoic" should be -- alkanoic --

Column 7, Line 25

"from" should be -- form --

Column 8, Line 50

3.23%H should be included in Calculation

Column 8, Line 58

"1,2-benzisoxa zole" should be -- 1,2-benzisoxazole --

Column 11, Line 32

"benzasoxazol" should be -- benzisoxazol --

UNITED STATES PATENT AND TRADEMARK OFFICE
CERTIFICATE OF CORRECTION

PATENT NO. : 4,504,669

DATED : March 12, 1985

INVENTOR(S) : Gregory M. Shutske

It is certified that error appears in the above-identified patent and that said Letters Patent is hereby corrected as shown below:

Column 12, Line 44

" -N-ethylproponamide" should be -- -N-ethylpropionamide --

Column 12, Line 54

"2,4,6-triflouromethyl- " should be -- 2,4,6-trifluoromethyl- --

Column 13 and 14, Reaction Scheme

-- wherein R, $R^1$, $R^2$, $R^3$, $R^4$, $R^5$, $R^6$, $R^7$, Y and n are as hereinbeforedescribed and M is alkali metal. -- should be included Signed and Sealed this Twenty-fourth Day of September 1985

[SEAL]

Attest:

DONALD J. QUIGG

Attesting Officer

Commissioner of Patents and Trademarks—Designate